US010407358B2

(12) United States Patent
Wei et al.

(10) Patent No.: US 10,407,358 B2
(45) Date of Patent: Sep. 10, 2019

(54) PROCESS FOR ETHYLENE OLIGOMERIZATION TO PRODUCE ALPHA-OLEFINS

(71) Applicant: Saudi Arabian Oil Company, Dhahran (SA)

(72) Inventors: Xu Wei, Dhahran (SA); Kareemuddin Shaik, Dhahran (SA); Zhonglin Zhang, Dhahran (SA); Rodrigo Sandoval Rivera, Thuwal (SA); Sohel Shaikh, Dhahran (SA); Hussain Yami, Thuwal (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 15/921,048

(22) Filed: Mar. 14, 2018

(65) Prior Publication Data
US 2018/0354870 A1    Dec. 13, 2018

Related U.S. Application Data

(60) Provisional application No. 62/471,266, filed on Mar. 14, 2017.

(51) Int. Cl.
*C07C 2/30* (2006.01)
*C07C 2/36* (2006.01)
(Continued)

(52) U.S. Cl.
CPC .............. *C07C 2/30* (2013.01); *B01J 21/08* (2013.01); *B01J 21/16* (2013.01); *B01J 31/143* (2013.01);
(Continued)

(58) Field of Classification Search
CPC . B01J 31/146; B01J 21/16; B01J 21/08; B01J 31/2404; B01J 31/143;
(Continued)

(56) References Cited

U.S. PATENT DOCUMENTS 4,020,121 A     4/1977 Kister et al.
4,242,531 A    12/1980 Carter
(Continued)

FOREIGN PATENT DOCUMENTS

EP     0181954 A1    5/1986
EP     0135441 B1   11/1986
(Continued)

OTHER PUBLICATIONS

Canivet et al.; "MOF-Supported Selective Ethylene Dimerization Single-Site Catalysts through One-Pot Postsynthetic Modification", J. Am. Chem. Soc. 2013, 135, 4195-4198. (Year: 2013).*
(Continued)

*Primary Examiner* — In Suk C Bullock
*Assistant Examiner* — Ali Z Fadhel
(74) *Attorney, Agent, or Firm* — Bracewell LLP; Constance G. Rhebergen; Kevin R. Tamm

(57) ABSTRACT

Described here are various processes for producing linear alpha olefins using a heterogeneous catalytic composition in the reaction mixture. These processes include size-based or phase-based separation of the heterogeneous catalytic compositions from the product stream and recycling the catalysts to the reaction mixture. Various other embodiments may be disclosed and claimed.

15 Claims, 3 Drawing Sheets

(51) Int. Cl.
*C07C 7/09* (2006.01)
*B01J 21/08* (2006.01)
*B01J 21/16* (2006.01)
*B01J 31/14* (2006.01)
*B01J 31/16* (2006.01)
*B01J 31/24* (2006.01)
*C07C 11/08* (2006.01)
*C07C 11/107* (2006.01)

(52) U.S. Cl.
CPC ......... *B01J 31/146* (2013.01); *B01J 31/1691* (2013.01); *B01J 31/2404* (2013.01); *C07C 2/36* (2013.01); *C07C 7/09* (2013.01); *B01J 2231/20* (2013.01); *C07C 2521/04* (2013.01); *C07C 2521/06* (2013.01); *C07C 2521/08* (2013.01); *C07C 2521/16* (2013.01); *C07C 2531/14* (2013.01); *C07C 2531/24* (2013.01); *Y02P 20/52* (2015.11)

(58) Field of Classification Search
CPC ..... B01J 31/1691; B01J 2231/20; C07C 7/09; C07C 31/24; C07C 2531/14; C07C 2/36; C07C 2531/24; C07C 2521/04; C07C 2521/06; C07C 2521/16; C07C 2521/08; Y02P 20/52
See application file for complete search history.

(56) References Cited

U.S. PATENT DOCUMENTS

| | | | |
|---|---|---|---|
| 4,484,016 A | | 11/1984 | Maschmeyer et al. |
| 4,538,018 A | | 8/1985 | Carter |
| 5,043,509 A | * | 8/1991 | Imai ........................ B01J 27/16 502/527.16 |
| 5,382,738 A | * | 1/1995 | Reagen ..................... C07C 2/30 502/117 |
| 7,964,763 B2 | | 6/2011 | Dixon et al. |
| 8,003,839 B2 | | 8/2011 | Buchanan et al. |
| 9,029,619 B2 | | 5/2015 | Vermeiren |
| 9,598,329 B2 | | 3/2017 | Shaik et al. |
| 2007/0185360 A1 | * | 8/2007 | Buchanan ................ C07C 2/32 585/521 |
| 2012/0310025 A1 | * | 12/2012 | Wang .................... B01J 31/188 585/511 |
| 2015/0203418 A1 | | 6/2015 | Meiswinkel et al. |
| 2015/0299069 A1 | | 10/2015 | Azam et al. |
| 2016/0289574 A1 | | 10/2016 | Timken et al. |
| 2017/0106358 A1 | | 4/2017 | Zhong et al. |
| 2017/0151547 A1 | | 6/2017 | Shaik et al. |
| 2017/0203288 A1 | | 7/2017 | Al-Hazmi et al. |
| 2017/0210680 A1 | | 7/2017 | Azam et al. |
| 2017/0349509 A1 | * | 12/2017 | Zilbershtein ............. C07C 2/30 |

FOREIGN PATENT DOCUMENTS

| | | |
|---|---|---|
| EP | 0200654 B1 | 11/1986 |
| EP | 2684857 A1 | 1/2014 |
| EP | 2738151 A1 | 6/2014 |

OTHER PUBLICATIONS

Clerici et al.; ("Liquid Phase Oxidation via Heterogeneous Catalysis: Organic Synthesis and Industrial Applications", section 10.4.1.2). (Year: 2013).*
International Search Report and Written Opinion for International Application No. PCT/US2018/022328; report dated May 16, 2018; 9 pages.
Farrell, L. M., "Developments in LAO Comonomer Technologies for Polyethylene"; PERP 2011S11 Report; May 2012, pp. 1-7.
Metzger, et al., "Selective Dimenzation of Ethylene to 1-Butene with a Porous Catalyst", American Chemical Society; Feb. 2016; vol. 2, pp. 148-153.
Smith, P. D., et al. "Ethylene dimerization over supported titanium alkoxides." Journal of Catalysis 105.1 (1987): 187-198.

* cited by examiner

PROCESS FOR ETHYLENE OLIGOMERIZATION TO PRODUCE ALPHA-OLEFINS

CROSS-REFERENCE TO RELATED APPLICATIONS

This application claims the benefit of U.S. Provisional Application No. 62/471,266, filed Mar. 14, 2017, which is incorporated herein by reference in its entirety.

FIELD

The disclosure relates to processes for ethylene oligomerization to produce alpha-olefins using heterogeneous catalysts.

BACKGROUND

Linear alpha olefins generally are important petrochemicals having a variety of uses. These chemicals have the general chemical formula $C_xH_{2x}$ and have a primary use as co-monomers for producing various polymers including polyethylene. Generally, linear alpha olefins are different from other mono olefins having a similar chemical formula, and these differences include linearity of the carbon chain and position of the double bond at the alpha position of the carbon chain in contrast to branched carbon chains and a double bond located at a beta-gamma position or higher of other mono olefins.

There are numerous processes for producing a variety of linear alpha olefins including ethylene oligomerization processes. Generally, existing processes for ethylene oligomerization are solution-based processes that operate in a liquid phase using a soluble catalyst system and do not depend on a solid catalyst. Some of these processes can include oligomerization processes such as Axens AlphaButol® process, Axens AlphaHexol™ process, Sasol's 1-octene process, and Shell's 1-butene process. These and other processes for producing linear alpha olefins may have problems associated with formation of undesired polymeric material that cause reactor fouling. Fouling can result in reactor shutdown for a cleanup, resulting in a loss of production and an increase of production costs. Additionally, various processes for production of alpha olefins use expensive catalysts to achieve high selectivity for certain reaction products, such as 1-hexene and 1-octene. These expensive catalysts often are unrecoverable and can be continuously discarded and disposed of during product recovery phases of production.

SUMMARY

Disclosed here are embodiments of compositions, methods, and systems for catalyst-mediated ethylene oligomerization to produce linear alpha olefins, all of which are directed to address the shortcomings of the art, including specific methods for providing catalysts in a solid form to the oligomerization reaction mixture. Also, disclosed here are methods of separating the unspent catalysts from the reaction product stream and recycling the unspent catalysts to the reaction mixture.

Embodiments disclosed and described herein include methods for producing linear alpha olefins using heterogeneous catalytic compositions. One such method includes the steps of contacting ethylene, in a reactor under oligomerization conditions, with a heterogeneous catalytic composition to produce a first product stream; recovering, from the reactor, the first product stream including linear alpha olefins, unreacted ethylene, spent catalytic composition fraction, and usable catalytic composition fraction; separating the usable catalytic composition fraction from the first product stream to produce a second product stream; recovering via fractionation of the second product stream at least one linear alpha olefin product; and recycling the usable catalytic composition fraction to the reactor. In certain embodiments, the heterogeneous catalytic composition includes a catalyst and a co-catalyst. The catalyst can be one or more of an aluminum-based catalyst and a transition metal-based catalyst. The transition metal in the transition metal-based catalyst is at least one member of the group consisting of nickel, titanium, zirconium or chromium. The catalyst can be one or more of a phosphorus-oxygen chelate of nickel (I) complex, a zirconium-aluminum alkyl halide, a tri-alkyl aluminum compound, a titanate-aluminum alkyl compound, a chromium(III) complex bearing imino-furfural ligands, a titanium butoxide—triethylaluminum compound, a cyclopentadienyl-arene complex, and other ethylene oligomerization catalysts. In certain embodiments, the co-catalyst is insoluble methylaluminoxane. The catalyst can be a metal-organic framework based catalyst. In certain embodiments, the co-catalyst is soluble methylaluminoxane. Certain embodiments of the catalytic compositions include a solid support. For example, the solid support can be silica, clay, zeolite, aluminosilicate, and combinations thereof. In certain embodiments, the solid support and the co-catalyst comprise methylaluminoxane. In certain embodiments, the co-catalyst is at least one member of the group consisting of boron-based complex and organoaluminum compounds represented by the formula $R_1R_2R_3A$, wherein A is either boron or aluminum, and $R_1$, $R_2$, and $R_3$ are hydrocarbyl groups with or without heteroatom substitutions. The co-catalyst can be $B(C_6F_5)_3$, $Ph_3C(B(C_6F_5)_4$, or $[PhMe_2NH][B(C_6F_5)_4]$ or salts thereof. In certain embodiments, the usable catalytic composition fraction is separated from the first product stream using a gravity-based separation process, such as centrifugation, or a particle size-based separation process, such as filtration or centrifugation, or a phase-based separation process.

Another embodiment of a method for producing linear alpha olefins includes the following steps: supplying a catalytic composition, containing a soluble catalyst and a soluble co-catalyst linked to a solid support, and ethylene to a reactor under oligomerization conditions, to produce a first product stream; recovering, from the reactor, the first product stream including linear alpha olefins, unreacted ethylene, spent catalytic composition fraction, and usable catalytic composition fraction; separating the usable catalytic composition fraction from the first product stream to produce a second product stream; recovering via fractionation of the second product stream at least one linear alpha olefin product; and recycling the usable catalytic composition fraction to the reactor. The usable catalytic composition fraction can be separated from the first product stream using a gravity-based separation process, such as, for example, centrifugation. The usable catalytic composition fraction can be separated from the first product stream using a particle size-based separation process, such as, for example, filtration or centrifugation. The usable catalytic composition fraction can be separated from the first product stream using a phase-based separation process. The solid support used in these methods can be silica, clay, zeolite, aluminosilicate, solid aluminoxane, and combinations thereof. The catalyst can be one or more of an aluminum-based catalyst and a transition metal-based catalyst. In certain embodiments, the co-catalyst can be a boron-based complex or an organoaluminum compounds represented by the formula $R_1R_2R_3A$, wherein A is either boron or aluminum, and $R_1$, $R_2$, and $R_3$ are hydrocarbyl groups with or without heteroatom substitutions. The boron based complex is at least one member of the group consisting of $B(C_6F_5)_3$, $Ph_3C(B(C_6F_5)_4$, and $[PhMe_2NH][B(C_6F_5)_4]$ or salts thereof.

Numerous other aspects, features and benefits of this disclosure may be made apparent from the following detailed description taken together with the drawing figures. The systems can include less components, more components, or different components depending on desired analysis goals. It should be further understood that both the foregoing general description and the following detailed description contain explanatory examples and are intended to provide further explanation of the embodiments as claimed.

BRIEF DESCRIPTION OF THE DRAWINGS

Embodiments will be readily understood by the following detailed description in conjunction with the accompanying drawings. To facilitate this description, like reference numerals designate like structural elements or procedures in a method. Embodiments are illustrated by way of example and not by way of limitation in the figures of the accompanying drawings.

DETAILED DESCRIPTION

Figure 1:
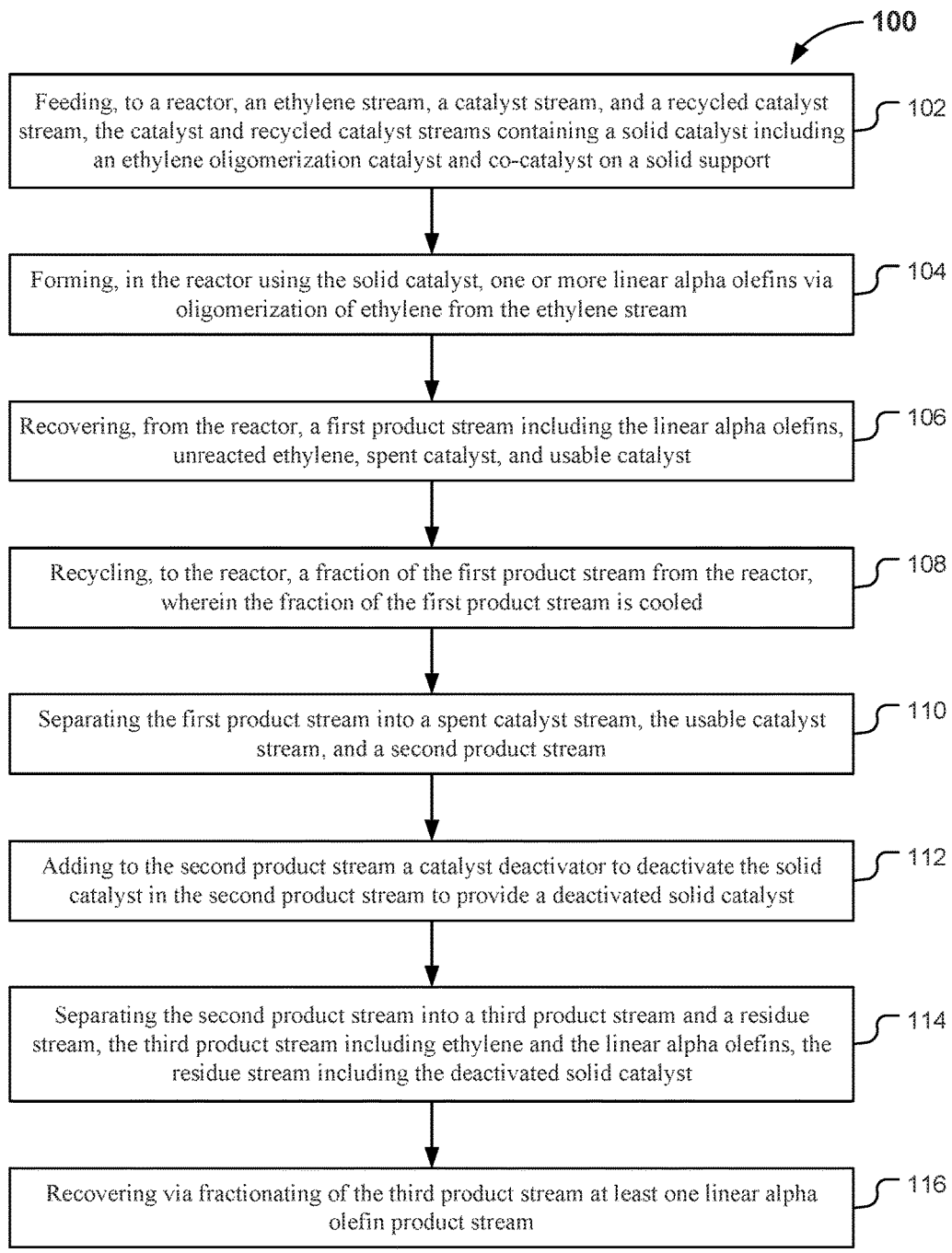
FIG. 1 schematically illustrates a method for producing linear alpha olefins, in accordance with various embodiments.

The present disclosure describes various embodiments related to processes, devices, and systems for ethylene oligomerization to produce alpha-olefins. In the following description, numerous details are set forth in order to provide a thorough understanding of the various embodiments. In other instances, well-known processes, units, and systems may not been described in particular detail in order not to unnecessarily obscure the various embodiments. Additionally, illustrations of the various embodiments may omit certain features or details in order to not obscure the various embodiments.

In the following detailed description, reference is made to the accompanying drawings that form a part of this disclosure. Like numerals may designate like parts throughout the drawings. The drawings may provide an illustration of some of the various embodiments in which the subject matter of the present disclosure may be practiced. Other embodiments can be utilized, and logical changes can be made without departing from the scope of this disclosure. Therefore, the following detailed description is not to be taken in a limiting sense.

The description may use the phrases "in various embodiments," "in an embodiment," or "in certain embodiments," which may each refer to one or more of the same or different embodiments. Furthermore, the terms "comprising," "including," "having," and the like, as used with respect to embodiments of the present disclosure, are synonymous.

The term "soluble" refers to the chemical property of a given substance (catalyst, co-catalyst, or support) to dissolve in a non-aqueous solvent such as hexane and toluene. A common threshold to describe a substance as soluble if more than 0.1 grams can be dissolved in 100 milliliters (mL) of non-aqueous solvent at 25° C. For example, titanium butoxide compounds such as $Ti(OBu)_4 \cdot nTHF$ (n=4-6) and aluminum catalysts like triethylaluminum (TEAL) are soluble in butene and other hydrocarbon solvents, while support components, such as silica, clay, and alumina, are insoluble in these hydrocarbon solvents. In certain embodiments, the titanium catalysts are soluble in organic solvent, while the co-catalyst such as solid methylaluminoxane (MAO) is insoluble. The catalyst system including the catalyst, the co-catalyst, and supports (optional) is insoluble in non-aqueous solvents and is present as a slurry in the reaction mixture.

The term "solid catalyst" refers to a catalytic composition that is present in the solid phase of at least two-phase solid/fluid reaction mixture. The catalytic composition is constructed using one or more of the following components linked together: (i) a transition metal-based catalyst, such as nickel, titanium, or chromium-based catalysts, (ii) an aluminum-based co-catalyst, such as trimethylaluminum, triethylaluminum, MAO, or a boron-based co-catalyst, such as $(C_6F_5)_3B$, $Ph_4N[B(C_6F_5)_4]$, and (iii) a support, such as silica, alumina, clay, polymers, or solid MAO. In certain embodiments, such as with solid MAO, the same component can serve as both a co-catalyst and a solid support. In an embodiment, the catalytic composition is insoluble in the reaction mixture and is present as a slurry.

A catalytic composition can be characterized as heterogeneous or homogenous based on the distribution of the catalyst in the reaction mixture. The catalytic composition is homogeneous if the catalytic composition is uniformly distributed in the reaction mixture and is heterogeneous if it is distinctly non-uniform in composition. In a homogeneous catalyst system, the catalyst is not readily separable from the rest of the species in the reaction mixture. For example, the Alphabutol® catalyst system (available from Axens, headquartered in Rueil-Malmaison, Paris, France) is homogeneous because the catalyst [$Ti(OBu)_4$] and co-catalyst (triethylaluminum) can dissolve in its solvent (1-butene) to form homogeneous solutions during the dimerization. The catalytic composition disclosed here is heterogeneous, because at least one of the catalyst components (catalyst, co-catalyst, or support) is sparingly soluble or insoluble in the reaction mixture and cannot form the uniform solution during the reaction. The use of the heterogeneous catalyst system as described here eliminates the need for a catalyst deactivation step. When homogeneous catalyst systems are present in solution, the ability of the catalyst to continue the reaction has to be stopped before the reaction mixture is supplied to downstream units. The reaction mixture with the active catalyst can pose a safety or operational hazard to the downstream process units. A catalyst deactivation step renders the catalysts no longer usable or available for recycling, without additional processing such as reactivation. Moreover, the catalyst being present as a homogeneous system cannot be recovered by mechanical separation steps.

The embodiments disclosed and described here relate to novel processes for ethylene oligomerization to produce 1-butene, 1-hexene, 1-octene, and other linear alpha olefins utilizing a solids-based catalytic system in contrast to a solution-based catalyst system. Embodiments can include solid supports for ethylene oligomerization catalysts and co-catalysts, including silica, clay, alumina-silica, zeolite, and other catalyst solid supports. Embodiments can include MAO as a solid support, where the MAO also functions as a co-catalyst in a heterogeneous catalytic system for ethylene oligomerization. Various embodiments can use a combination of solid supports.

Embodiments described and disclosed here can have several advantages over a solution-based system, including recovery and recycling of unspent solid catalysts to the reactor to provide cost-savings and removal of polymer formed during the process via attachment to the solid catalyst system. The spent catalytic composition fraction with polymer can be removed from the process to prevent buildup of polymer in the process. This removal of the polymer can reduce or prevent deposition of polymer on reactor surfaces, thus reducing reactor fouling. The solid support can act as a fouling scavenger by scavenging the polymer to prevent deposition on the reactor surfaces. The solid catalyst system can be constructed from a soluble catalyst and a soluble co-catalyst attached to a solid support. For example, a silica support is first allowed to react with a soluble MAO, and then combination of silica-MAO is reacted in the presence of soluble titanium catalysts. This silica-MAO-titanium catalyst system is delivered to the ethylene-containing reaction mixture, which leads to higher activity of ethylene oligomerization. Another example is a catalytic composition containing a soluble catalyst Ti(OBu)$_4$.nTHF (n=4-6), soluble co-catalyst TEAL and insoluble support. The co-catalyst reacts with the support via trace amount of hydroxyl groups on the support surface and binds to the surface. Once the co-catalyst activates the catalyst, the catalyst binds into surface as well to form the solid support catalytic composition. In another embodiment, a soluble catalyst interacts with an insoluble co-catalyst that is attached to a solid support. In another embodiment, a soluble catalyst interacts first with an insoluble co-catalyst, and then the linked catalyst-co-catalyst entity is attached to a solid support to form a catalytic composition. In another embodiment, a soluble catalyst and an insoluble co-catalyst form the catalytic composition. For example, a soluble Ti catalyst and insoluble solid MAO form the catalytic composition. The MAO component is made of 10-100 micron particles and functions as both support and activator of catalyst.

Various embodiments can use a series of equipment for solid-liquid separation to recover spent and partially spent catalytic composition fraction, as well as recycle the usable recovered catalyst. The spent catalytic composition fractions and the unused catalysts differ in size in this system and this size difference can be exploited to separate the two from the reaction mixture. For example, in an embodiment, the active catalytic composition and the unspent or usable catalytic composition have a size distribution less than 30 micrometers (µm), while the spent catalytic composition has a size distribution ranging from 30 µm to 500 µm. Examples of separation equipment can include filters, sieves, strainers, bag filters, nanofiltration devices, centrifuges, and various combinations of these units. The spent catalytic composition can be removed from the various process streams. Various embodiments can use various separation devices and techniques to recover alpha-olefin products, unreacted ethylene for recycling, and a solvent for recycling when the solvent is used in the various processes. Various separation devices and techniques can be used for further purification of alpha-olefin product streams, including tanks, evaporation units, condensation units, and fractionation units such as packed or tray columns.

Figure 2:
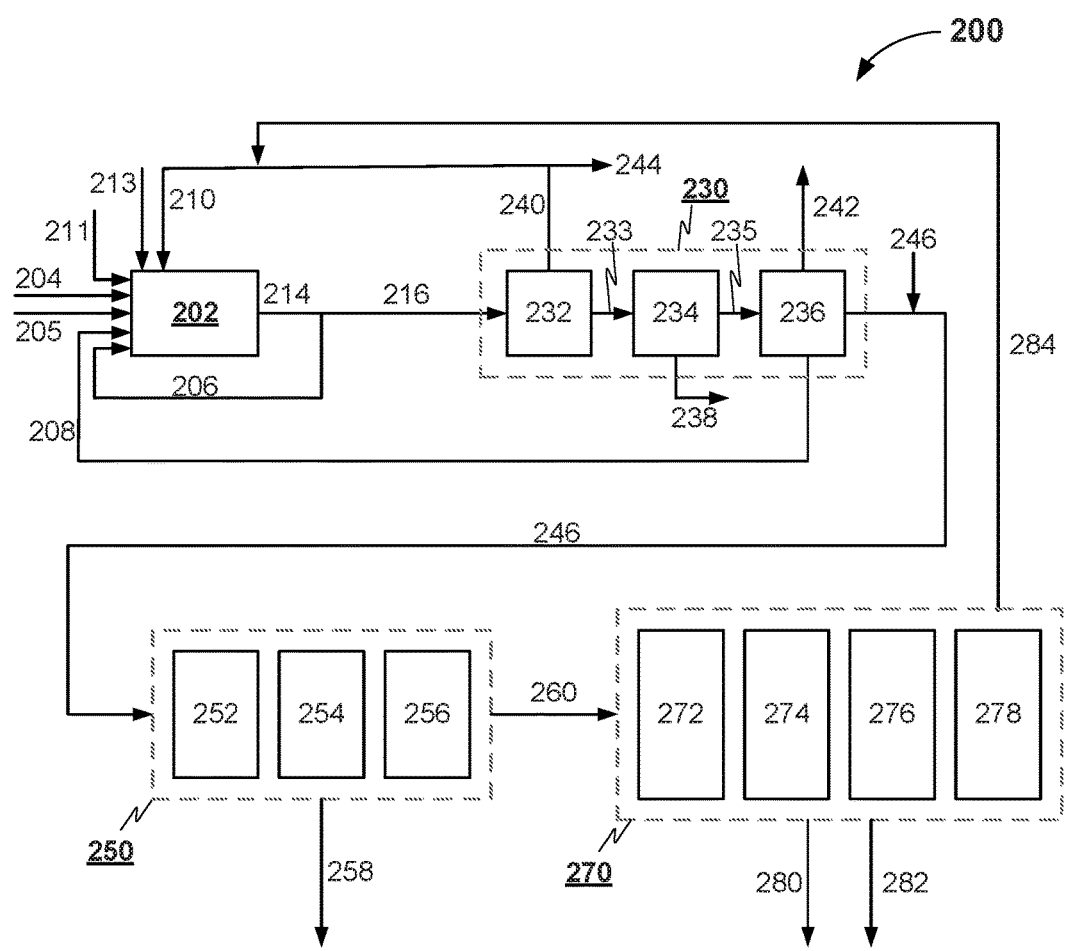
FIG. 2 schematically illustrates a system for producing linear alpha olefins, in accordance with various embodiments.
Figure 3:
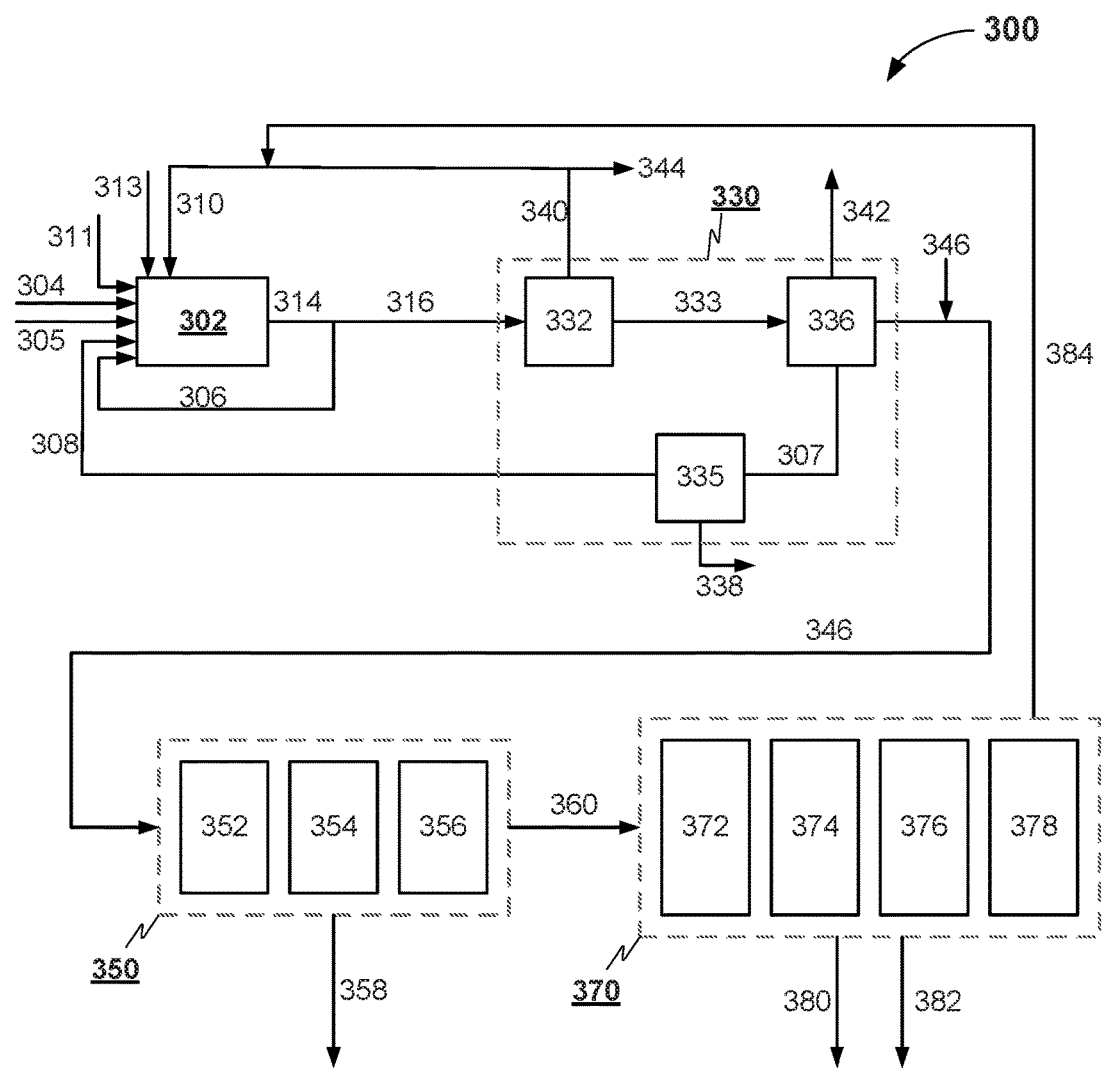
FIG. 3 schematically illustrates an alternative system for producing linear alpha olefins, in accordance with various embodiments.

FIGS. 1-3 are described together for better understanding of the method of FIG. 1, as implemented in the process diagrams of FIGS. 2 and 3. FIG. 1 schematically illustrates a method 100 for producing linear alpha olefins, in accordance with various embodiments.

At step 102 of process 100 in FIG. 1, the process includes feeding, to a reactor, an ethylene stream, a catalyst stream, and a recycled catalyst stream. The catalyst stream and the recycled catalyst stream contain a solid catalytic composition that can include an ethylene oligomerization catalyst and co-catalyst on a solid support. In various embodiments, the solid support can also function as a co-catalyst. The catalyst and co-catalyst can be coupled to the solid support by chemical bonds, by physical adsorption, or by both chemical bonds and physical adsorption. The coupling is sufficiently strong to allow the catalyst and co-catalyst to remain coupled during an ethylene oligomerization reaction in a reactor followed by subsequent processing to recover and recycle the solid catalyst to the reactor for further ethylene oligomerization reactions. In various embodiments, well-known methods may be used to couple an ethylene oligomerization catalyst and co-catalyst to a solid support. In various embodiments, an incipient wetness process can be used for coupling of an ethylene oligomerization catalyst and co-catalyst to a solid catalyst. In various embodiments, a mole ratio of catalyst to co-catalyst can be from 1-500. In various embodiments, the catalyst and co-catalyst for ethylene oligomerization can be coupled to a solid support such as silica, alumina-silicate, zeolite, metal oxide, clay, and polymer. In an embodiment, a solid support such as MAO can also function as a co-catalyst. In another embodiment, the solid support can be polystyrene.

The process 100 can include the step 104 of forming, in the reactor using the solid catalyst, one or more linear alpha olefins via oligomerization of ethylene from the ethylene stream. The reactor can be a vertical pressure vessel. An internal agitator can be included in the reactor. For example, the internal agitator can be a central stirrer on an axis powered by a motor. In various embodiments, the reactor can be a plug flow reactor. In various embodiments, the reactor can be an oscillatory baffled reactor. In various embodiments, internal cooling of the reactor may be absent due to potential maintenance issues. For example, if a polymeric material deposits on an internal cooling tube, efficiency of cooling can reduce significantly, causing production issues. In various embodiments, the temperature inside the reactor during operation can range from 30° C. to 200° C. In other embodiments, the temperature inside the reactor during operation can range from 30° C. to 150° C. In other embodiments, the temperature inside the reactor during operation can range from 30° C. to 100° C. In other embodiments, the temperature inside the reactor during operation can range from 30° C. to 80° C. In various embodiments, the pressure inside the reactor during operation can range from 5 to 90 bar gauge. In other embodiments, the pressure inside the reactor during operation can range from 20 to 40 bar gauge.

The process 100 can include the step 106 of recovering, from the reactor a first product stream including the linear alpha olefins, unreacted ethylene, and the solid catalytic composition. The first product stream can be a mixed phase stream including solid, liquid, and gas phases. The gas can be dissolved in the liquid or can be a mixed phase stream of solid and liquid with gas dissolved in the liquid. The gas can be predominantly ethylene.

The process 100 can include the step 108 of recycling to the reactor a fraction of the first product stream from the reactor. In certain embodiments, the fraction of the first product stream is cooled. In various embodiments, this fraction of the first product stream can be recycled to the reactor using a pump around system. The pump around system can be used to remove the reaction heat generated during the ethylene oligomerization reaction in the reactor. In various embodiments, the pump around system can include one or more pumps and heat exchangers for cooling the fraction of the first product stream from the reactor before recycling the stream to the reactor. In various embodiments, one or more heat exchangers can use cooling water to remove reaction heat. In various embodiments, the fraction of the first product stream can be fed separately to the reactor from other streams fed to the reactor. In various embodiments, a flowrate of the fraction of the first product stream can be determined by a reaction residence time requirement of the reactor.

The process 100 can include the step 110 of separating the remainder of the first product stream into a spent catalytic composition stream, the usable catalytic composition stream, and a second product stream. The spent catalytic composition stream and the usable catalytic composition stream can be separated based on size of the particles. For example, in an embodiment, the active catalytic composition and the unspent or usable catalytic composition have a size distribution less than 30 μm, while the spent catalytic composition has a size distribution of about 30 μm and 50 μm. This size distribution is exploited to separate the particles and produce the second product stream. The process 100 can include an optional step 112 of adding to the second product stream a catalyst deactivator to deactivate the solid catalyst in the second product stream, thus producing a deactivated solid catalyst. In various embodiments, the catalyst deactivator can be an alcohol, an amine, or water or any other suitable deactivator. Example alcohols can include methanol, ethanol, butanol, and glycol. Example amines can include ammonia and $RNH_2$, where R is a hydrocarbyl.

The process 100 can include the step 114 of separating the second product stream into a third product stream and a residue stream. The third product stream includes ethylene and the linear alpha olefins, while the residue stream includes the deactivated solid catalyst. The process 100 can include the step 116 of recovering via fractionating of the third product stream at least one linear alpha olefin product stream. In various embodiments, additional linear alpha olefin product steams can be recovered. In various embodiments, an ethylene stream can be recovered for recycling to the reactor.

FIG. 2 schematically illustrates a system 200 for producing linear alpha olefins, in accordance with various embodiments. The system 200 includes a reactor 202 that has the following inputs: an ethylene stream 204, a catalyst stream 205, and a usable catalytic composition stream 208. In certain embodiments, the catalyst stream 205 and the co-catalyst stream 213 can be two independent streams that combine inside the reactor 202 to form the heterogeneous catalytic composition. In other embodiments, there is no co-catalyst stream 213 entering the reactor, and the catalyst stream 205 can contain the solid catalytic composition including an ethylene oligomerization catalyst and co-catalyst linked to a solid support. In certain embodiments, the usable catalytic composition stream 208 contains a solid catalytic composition including an ethylene oligomerization catalyst and co-catalyst linked to a solid support, and can enter the reactor 202 as an independent stream 208 as shown in FIG. 2 or can join the catalyst stream 205 before entry into the reactor 202. In various embodiments, the solid support can also function as a co-catalyst. The catalyst and co-catalyst can be coupled to the solid support by chemical bonds, by physical adsorption, or by both chemical bonds and physical adsorption. The coupling is sufficiently strong to allow the catalyst and co-catalyst to remain coupled during an ethylene oligomerization reaction in the reactor 202 followed by subsequent processing to recover and recycle the solid catalyst to the reactor 202 for further ethylene oligomerization reactions.

In various embodiments of system 200, the ethylene stream entering the reactor can include both a feedstock ethylene stream 204 and a usable ethylene stream 210. In other embodiments, a feedstock ethylene stream 204 and a recycled ethylene stream 210 can enter the reactor as two separate streams. The recycled ethylene stream 210 includes at least one of (a) a first recovered ethylene stream 240 from further separating of the first product stream or (b) a second recovered ethylene stream 284 from further fractionation process 270 of the third product stream 260. In various embodiments, the ethylene stream 204 can be fed to reactor 202 based on the amount of ethylene consumed in the reactor 202 as indicated by a pressure regulator (not shown). In various embodiments, the pressure inside the reactor 202 during operation can range from 5 to 100 bar gauge, and the feed rate of the ethylene stream 204 can be adjusted to maintain the pressure within the pressure range. In various embodiments, the ethylene stream 204, the catalyst stream 205, and the usable catalytic composition stream 208 can be fed to the reactor 202 separately from each other or in various combinations of combined streams. In various embodiments, the catalyst stream 205 and co-catalyst stream 213 can be fed separately to the reactor 202 or fed together as a single stream to the reactor 202. In various embodiments, the ethylene stream 204 can be fed to the reactor separately from the other streams or combined with the recycled ethylene stream 210.

The inputs to the reactor 202 can further include a solvent stream 211. In certain embodiments, the solvent stream can be fed separately to the reactor 202 from the ethylene stream 204, the catalyst stream 205, and the recycled catalyst stream 208. In various embodiments, the solvent stream 211 can include one or more of $C_3$ to $C_{10}$ hydrocarbons. The solvent stream 211 can include toluene or cyclohexane. The solvent stream can be toluene or cyclohexane and impurities in an amount that is within reasonable process tolerances. In certain embodiments, the solvent stream 211 can be fed to the reactor 202 with the catalyst stream 205 or a co-catalyst stream 213. In various embodiments, an amount of solvent can be approximately 0-90% by weight of the reaction fluids.

After the ethylene oligomerization process proceeds to produce one or more of 1-butene, 1-hexene, 1-octene, and other linear alpha olefins, a first product stream 214 is recovered from the reactor 202, and it contains linear alpha olefins, unreacted ethylene, and the solid catalyst. The first product stream 214 can be a mixed phase stream including solid, liquid, and gas with gas dissolved in the liquid or can be a mixed phase stream of solid and liquid with gas dissolved in the liquid. The gas can be predominantly ethylene. A fraction of the first product stream 214 is recycled via stream 206 to the reactor. In certain embodiments, the fraction stream 206 from the first product stream 214 is cooled. In certain embodiments, the fraction stream 206 of the first product stream 214 can be recycled to the reactor 202 using a pump around system. The pump around system can remove the reaction heat generated during the ethylene oligomerization reaction in the reactor 202. The pump around system can include one or more pumps and heat exchangers for cooling the fraction stream 206 of the first product stream 214 before recycling the stream to the reactor 202. In various embodiments, the fraction stream 206 from the first product stream 214 can be fed separately to the reactor 202 from other streams fed to the reactor. In various embodiments, a flowrate of the fraction stream 206 can be determined by a reaction residence time requirement of the reactor 202. In some embodiments, the fraction stream 206 recycled to the reactor 202 can be 95 to 99% by weight of the first product stream 214, while the remainder product stream 216 from the first product stream is about 1-5% and is processed further downstream for recovery of ethylene, solid catalyst, and linear alpha olefins. In various embodiments, the fraction stream 206 recycled to the reactor 202 can be approximately 98% by weight of the first product stream 214, with the remainder stream 216 from the first product stream to be processed further downstream for recovery of ethylene, solid catalyst, and linear alpha olefins.

The remainder stream 216 from the first product stream 214 is then subjected to one or more solid/fluid separation processes. For example, the remainder stream 216 from the first product stream 214 is subjected to flashing in a vapor-liquid separator, such as a flash drum 232 to recover a first recycled ethylene stream 240 and a flashed first product stream 233.

In certain embodiments, the flash drum (surge drum) 232 can operate to hold ethylene in the flash drum under normal operating conditions. In other embodiments, pressure in the flash drum 232 can reach a predetermined level in which ethylene can be vented from the flash drum 232 to prevent pressure from further increasing in the flash drum 232. In various embodiments, vented ethylene can be recovered and recycled to the reactor 202. The flashed first product stream 233 is then subject to a solid/fluid separation unit 234 to separate the spent catalytic composition stream 238 and a filtered first product stream 235. In various embodiments, the spent catalytic composition stream 238 can comprise approximately 5-100% of the catalyst in the first product stream 216. A second separation unit 236 is placed downstream of the solid/fluid separation unit 234 to process the filtered first product stream 235 and produce the second product stream 246 and the usable catalytic composition stream 208.

In various embodiments, an ethylene stream 242 can be vented from the second separation unit 236. In other embodiments, this ethylene stream 242 can be recovered and recycled at least in part to provide another source of recycled ethylene. In various embodiments, the spent catalytic composition stream 238 from the first separation unit is separated based on size. For example, the spent catalytic composition stream 238 can comprise catalyst particles greater than an effective diameter of approximately 30-50 µm. Although the spent catalytic composition particles may not be spherical, these particles may have an effective diameter equivalent to a sphere for separation purposes. In other words, the spent catalytic composition particles may separate in a separation unit similar to a spherical particle having a diameter greater than approximately 30-50 µm. In certain embodiments, a majority of the catalyst from the first product stream 216 can be in the usable catalytic composition stream 208. A strainer or a bag filter, for example, can be used in the separation unit 234 and can be used for separating the flashed first product stream 233 to provide the spent catalytic composition stream 238 and a filtered first product stream 235. In certain embodiments, a phase separator, centrifuge, or clarification tank can be the second separation unit 236 and can be used for separating the filtered first product stream 235 to provide the second product stream 246 and the usable catalytic composition stream 208.

In certain embodiments, the second product stream 246 is separated into the third product stream 260 and the residue stream 258 using a separation system 250. In an embodiment, this separation system 250 includes an evaporator 252, a condenser 254, and a surge drum 256. In this embodiment, the second product stream 246 is subject to evaporation in an evaporator 252 to produce a vapor stream including ethylene and the linear alpha olefins and the residue stream 258. The vapor stream is then passed through the condenser 254 to provide the third product stream 260. The third product stream 260 is collected in a surge drum 256. In various embodiments, the evaporator 252 can be used to separate the valuable liquid and gaseous constituents in the second product stream 246 from various impurities including the deactivated catalyst. The separated liquid and gaseous constituents can be further processed to recover ethylene, linear alpha-olefins, and solvent to be used in the ethylene oligomerization process. In various embodiments, the evaporator 252 can be heated by a heating-jacket. Ethylene, alpha-olefins products, and solvent can be vaporized and exit from the top of the evaporator. The residue stream 258, which can be a concentrated solution of impurities, can be drawn from the bottom of the evaporator 252. A feed to residue ratio can be controlled to minimize the loss of linear alpha olefins and solvent to the residue stream 258.

In certain embodiments, ethylene in the second product stream 246 remains in the third product stream 260 and is subject to separation via further downstream processes 270. In certain embodiments, the residue stream 258 can include a concentrated solution of deactivated catalyst, and this stream can be drained continuously from the bottom of the evaporator. In various embodiments, no additional solid-liquid separation unit can be included in the separating of the second product stream process.

In certain embodiments, the third product stream 260 is subject to the fractionation process 270 to produce at least one linear alpha olefin product stream 280. Fractionation of the third product stream 260 in first fractionation unit 272 leads to the production of a recycled ethylene stream 284 and a first effluent stream, followed by a subsequent fractionation of the first effluent stream in second fractionation unit 274 to recover a 1-butene stream and a second effluent stream. The second effluent stream is fractionated in third fractionation unit 276 to recover a 1-hexene stream and a third effluent stream; followed by a subsequent fractionation of the third effluent stream in fourth fractionation unit 278 to recover a solvent recycle stream 282 and a fourth effluent stream. The solvent in the solvent recycle stream 282 is sent to the solvent stream 211 that is fed to the reactor 202; and the fourth effluent stream is fractionated to recover 1-octene and a heavy fraction stream. In various embodiments, fractionation can occur in a distillation train. In various embodiments, a first column of the distillation train can be used to recover ethylene and can be configured to recycle the recovered ethylene to the reactor. In various embodiments, the solvent recycle stream can be fed to reactor 202 or combined with solvent stream 211 and fed to the reactor 202. In various embodiments, the various fractionators for fractionating can be packed or tray columns or a combination of packed and tray columns.

FIG. 3 schematically illustrates an alternative system 300 for producing linear alpha olefins, in accordance with various embodiments. In this embodiment, the spent catalytic composition and the usable catalytic composition are separated further downstream compared to the system 200. The system 300 includes a reactor 302 that has the following inputs: an ethylene stream 304, a catalyst stream 305, and a usable catalytic composition stream 308. In certain embodiments, the catalyst stream 305 and the co-catalyst stream 313 can be two independent streams that combine inside the reactor 302 to form the solid catalytic composition. In other embodiments, there is no co-catalyst stream 313 entering the reactor, and the catalyst stream 305 contains the solid catalytic composition including an ethylene oligomerization catalyst and co-catalyst linked to a solid support. In certain embodiments, the usable catalytic composition stream 308 contains a solid catalytic composition including an ethylene oligomerization catalyst and co-catalyst linked to a solid support, and can enter the reactor 302 as an independent stream as shown in FIG. 3 or can join the catalyst stream 305 before entry into the reactor 302.

In certain embodiments of system 300, the ethylene stream entering the reactor 302 can include a combination of a feedstock ethylene stream 304 and a recycled ethylene stream 310. The recycled ethylene stream 310 includes at least one of (a) a first recovered ethylene stream 340 from further separating of the first product stream or (b) a second recovered ethylene stream 384 from further fractionation process 370 of the third product stream 360. In various embodiments, the ethylene stream 304 can be fed to reactor 302 based on the amount of ethylene consumed in the reactor 302 as indicated by a pressure regulator (not shown). In various embodiments, the pressure inside the reactor 302 during operation can range from 5-100 bar gauge, and the feed rate of the ethylene stream 304 can be adjusted to maintain the pressure within the pressure range. In various embodiments, the ethylene stream 304, the catalyst stream 305, and the usable catalytic composition stream 308 can be fed to the reactor 302 separately from each other or in various combinations of combined streams. In various embodiments, the ethylene stream 304 can be fed to the reactor separately from the other streams or combined with the recycled ethylene stream 310.

The inputs to the reactor 302 can further include a solvent stream 311. In certain embodiments, the solvent stream can be fed separately to the reactor 302 from the ethylene stream 304, the catalyst stream 305, and the usable catalytic composition stream 308. In various embodiments, the solvent stream 311 can include one or more of $C_3$ to $C_{10}$ hydrocarbons. The solvent stream 311 can include toluene or cyclohexane. The solvent stream 311 can be toluene or cyclohexane and impurities in an amount that is within reasonable process tolerances. In certain embodiments, the solvent stream 311 can be fed to the reactor 302 with the catalyst stream 305 or a co-catalyst stream 313. In various embodiments, an amount of solvent can be approximately 0-90% by weight of the reaction fluids.

After the ethylene oligomerization process proceeds to produce one or more of 1-butene, 1-hexene, 1-octene, and other linear alpha olefins, a first product stream 314 is recovered from the reactor 302, and it contains linear alpha olefins, unreacted ethylene, and the solid catalyst. The first product stream 314 can be a mixed phase stream including solid, liquid, and gas with gas dissolved in the liquid or can be a mixed phase stream of solid and liquid with gas dissolved in the liquid. The gas can be predominantly ethylene. A fraction of the first product stream 314 is recycled via stream 306 to the reactor. In certain embodiments, the fraction stream 306 from the first product stream 314 is cooled. In various embodiments, the fraction stream 306 from the first product stream 314 can be fed separately to the reactor 302 from other streams fed to the reactor or combined with any of the input streams. In various embodiments, a flowrate of the fraction stream 306 can be determined by a reaction residence time requirement of the reactor 302. In some embodiments, the fraction stream 306 recycled to the reactor 302 can be 95 to 99% by weight of the first product stream 314, with the remainder stream 316 from the first product stream can be about 1 to 5% and is processed further downstream for recovery of ethylene, solid catalyst, and linear alpha olefins. In various embodiments, the fraction stream 306 recycled to the reactor 302 can be approximately 98% by weight of the first product stream 314, with the remainder stream 316 from the first product stream to be processed further downstream for recovery of ethylene, solid catalyst, and linear alpha olefins.

The remainder stream 316 from the first product stream 314 is then subjected to one or more solid/fluid separation processes. For example, the remainder stream 316 from the first product stream 314 is subjected to flashing in a vapor-liquid separator, such as a flash drum 332 to recover a first recycled ethylene stream 340 and a flashed first product stream 333.

The process of separating the first product stream 316 into the spent catalytic composition stream 338, the usable catalytic composition stream 308, and the second product stream 346 is carried out by separation units 330, and includes flashing the first product stream 316 in a flash drum 332 to recover a first recycled ethylene stream 340. The flashed first product stream 333 is then fed to a first separation unit 336 to produce the second product stream 346 and an exit catalyst stream 307. The exit catalyst stream 307 is fed to a second separation unit 335 to produce the spent catalytic composition stream 338 and the usable catalytic composition stream 308. In various embodiments, an ethylene stream 342 can be vented from the first separation unit 336 or can be recovered and recycled at least in part to provide another source of recycled ethylene. In various embodiments, the spent catalytic composition stream 338 can include catalyst particles greater than an effective diameter of approximately 10-100 µm. In various embodiments, the spent catalytic composition stream 338 can include catalyst particles greater than an effective diameter of approximately 30-100 µm. Although the spent catalytic composition particles may not be spherical, these particles may have an effective diameter equivalent to a sphere for separation purposes. In other words, the spent catalytic composition particles may separate in a separation unit similar to a spherical particle having a diameter greater than approximately 30-100 µm. In various embodiments, a majority of the catalyst from the first product stream 316 can be in the usable catalytic composition stream 308. In various embodiments, a strainer or a bag filter, for example, can be the second separation unit 335. In various embodiments, a phase separator, centrifuge, or clarification tank can be the first separation unit 336. In various embodiments, an ethylene stream 342 can be vented from the second separation unit 336. In other embodiments, this ethylene stream 342 can be recovered and recycled at least in part to provide another source of recycled ethylene. In various embodiments, the spent catalytic composition stream 338 is separated from the usable catalytic composition stream based on particle size. For example, the spent catalytic composition stream 338 can include catalyst particles greater than an effective diameter of approximately 30-500 µm. Although the spent catalytic composition particles may not be spherical, these particles may have an effective diameter equivalent to a sphere for separation purposes. In other words, the spent catalytic composition particles may separate in a separation unit similar to a spherical particle having a diameter greater than approximately 30-500 µm. In certain embodiments, a majority of the catalyst from the first product stream 316 can be in the usable catalytic composition stream 308. A strainer or a bag filter, for example, can be used in the separation unit 335 and can be used for separating the exit catalyst stream 307 to provide the spent catalytic composition stream 338 and a usable catalytic composition stream 308. In certain embodiments, a phase separator, centrifuge, or clarification tank can be the second separation unit 335 and can be used for separating the exit catalyst stream 307 to provide the spent catalytic composition stream 338 and a usable catalytic composition stream 308.

In certain embodiments, the second product stream 346 is separated into the third product stream 360 and the residue stream 358 using a separation system 350. In an embodiment, this separation system 350 includes an evaporator 352, a condenser 354, and a surge drum 356. In this embodiment, the second product stream 346 is subject to evaporation in an evaporator 352 to produce a vapor stream including ethylene and the linear alpha olefins and the residue stream 358. The vapor stream is then passed through the condenser 354 to provide the third product stream 360. The third product stream 360 is collected in a surge drum 356. In various embodiments, the evaporator 352 can be used to separate the valuable liquid and gaseous constituents in the second product stream 346 from various impurities including the deactivated catalyst. The separated liquid and gaseous constituents can be further processed to recover ethylene, linear alpha-olefins, and solvent to be used in the ethylene oligomerization process. In various embodiments, the evaporator 352 can be heated by a heating-jacket. Ethylene, alpha-olefins products, and solvent can be vaporized and exit from the top of the evaporator. The residue stream 358, which can be a concentrated solution of impurities, can be drawn from the bottom of the evaporator 352. A feed to residue ratio can be controlled to minimize the loss of linear alpha olefins and solvent to the residue stream 358.

In certain embodiments, ethylene in the second product stream 346 remains in the third product stream 360 and is subject to separation via further downstream processes 370. In certain embodiments, the residue stream 358 can include a concentrated solution of deactivated catalyst, and this stream can be drained continuously from the bottom of the evaporator. In various embodiments, no additional solid-liquid separation unit is included in the separation of the second product stream process.

In certain embodiments, the third product stream 360 is subject to the fractionation process 370 to produce at least one linear alpha olefin product stream 380. Fractionation of the third product stream 360 in first fractionation unit 372 leads to the production of a recycled ethylene stream 384 and a first effluent stream, followed by a subsequent fractionation of the first effluent stream in second fractionation unit 374 to recover a 1-butene stream and a second effluent stream. The second effluent stream is fractionated in third fractionation unit 376 to recover a 1-hexene stream and a third effluent stream; followed by a subsequent fractionation of the third effluent stream in fourth fractionation unit 378 to recover a solvent recycle stream 382 and a fourth effluent stream. The solvent in the solvent recycle stream 382 is sent to the solvent stream 311 that is fed to the reactor 302; and the fourth effluent stream is fractionated to recover 1-octene and a heavy fraction stream. In various embodiments, fractionation can occur in a distillation train. In various embodiments, a first column of the distillation train can be used to recover ethylene and can be configured to recycle the recovered ethylene to the reactor. In various embodiments, the solvent recycle stream can be fed back to reactor 302 or combined with solvent stream 311 and fed to the reactor 302. In various embodiments, the various fractionators for fractionating can be packed or tray columns or a combination of packed and tray columns.

In certain embodiments, the ethylene oligomerization catalyst and co-catalyst can be selective for a specific linear alpha olefin. In various embodiments, the ethylene oligomerization catalyst and co-catalyst can be non-selective with respect to a specific linear alpha olefin. Generally, non-selective ethylene oligomerization catalysts can produce a broad range of alpha oligomers ($C_6$ thru $C_{30+}$) with Shultz-Flory distributions and low selectivities towards one or more short chain linear alpha olefins.

In various embodiments, the ethylene oligomerization catalyst and co-catalyst can be a non-selective catalyst such as a phosphorus-oxygen chelate of nickel (I) and a boron hydride reducing agent. For example, the phosphorus-oxygen chelate of nickel (I) and the boron hydride reducing agent can be a catalyst system used in a Shell higher olefin process (SHOP). An example of the phosphorus-oxygen chelate of nickel (I) can include Formula I.

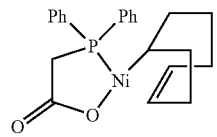

[Formula I]

In various embodiments, the ethylene oligomerization catalyst and co-catalyst can be a non-selective catalyst such as a zirconium-aluminum alkyl halide used in Sabic-Linde's Sablin process.

In various embodiments, the ethylene oligomerization catalyst and co-catalyst can be a non-selective catalyst such as a tri-alkyl aluminum ($AlR_3$) used in a Chevron-Phillips AlphaPlus process. In various embodiments, R can be ethyl.

In various embodiments, the ethylene oligomerization catalyst and co-catalyst can be a selective catalyst such as a titanate-aluminum alkyl catalyst used in an Alphabutol process.

In various embodiments, the ethylene oligomerization catalyst and co-catalyst can be a selective catalyst such as a trimerization catalyst used in a Chevron-Phillips process. Examples of trimerization catalysts are illustrated by Formulas II, III, and IV.

Phillips catalyst Generation I

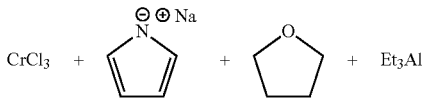

[Formula II]

Phillips catalyst Generation II

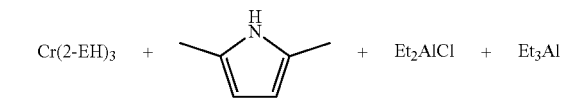

[Formula III]

Activity: 156 666 g/g Cr h
S(1-C6): 93.2%

Mitsubishi improved protocol

[Formula IV]

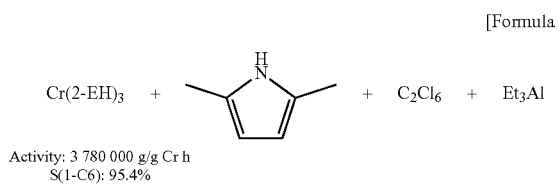

Activity: 3 780 000 g/g Cr h
S(1-C6): 95.4%

In various embodiments, the ethylene oligomerization catalyst and co-catalyst can be a selective catalyst such as a trimerization catalyst used in a British Petroleum process. An example of this catalyst can be p-orthomethoxy aryl P^N^P ligand with chromium and activated with methylalumoxane. Formulas V and IV illustrate this catalyst system.

BP catalyst

[Formula V]

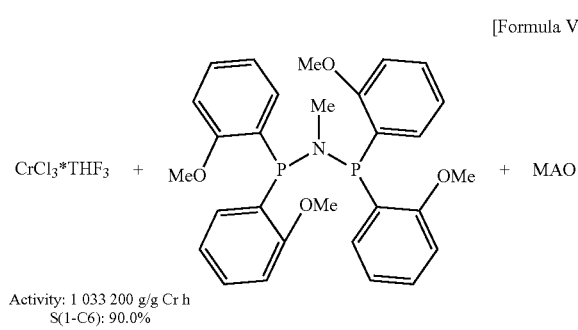

Activity: 1 033 200 g/g Cr h
S(1-C6): 90.0%

[Formula VI]

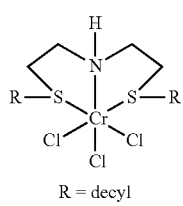

R = decyl

In various embodiments, the ethylene oligomerization catalyst and co-catalyst can be a selective catalyst such as a $(BuO)_4Ti$-Triethylaluminum (TEAL) catalyst system used in Axens AlphaHexol™ ethylene trimerization process.

In various embodiments, the ethylene oligomerization catalyst and co-catalyst can be a selective catalyst such as the catalyst system of Formula VII used in Sinopec's ethylene trimerization process.

[Formula VII]

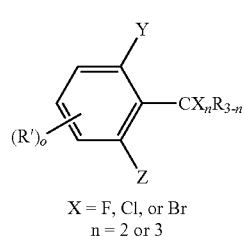

X = F, Cl, or Br
n = 2 or 3

In various embodiments, the ethylene oligomerization catalyst and co-catalyst can be a selective catalyst such as the catalyst system illustrated by Formulas VIII-XII used in Mutsui's ethylene trimerization process.

[Formula VIII]

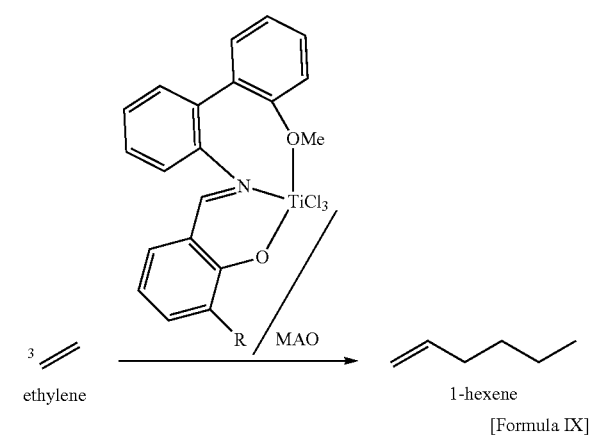

[Formula IX]

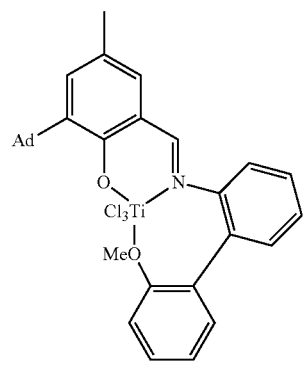

[Formula X]

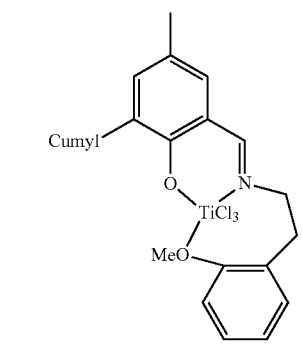

[Formula XI]

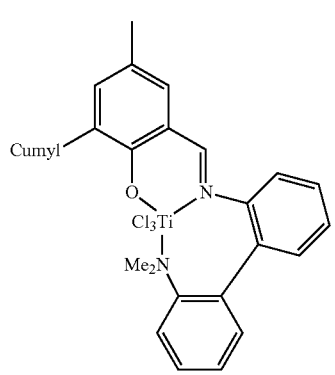

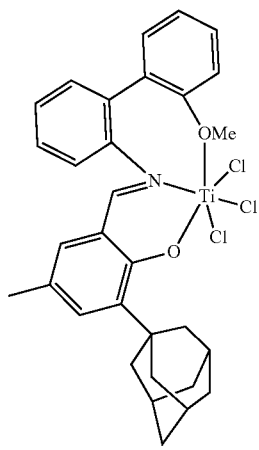

In various embodiments, the ethylene oligomerization catalyst and co-catalyst can be a selective catalyst such as a cyclopentadienyl-arene ligand system used in Decker's process. An example catalyst can be [Ind-(bridge)-Ar]TiCl₃ as illustrated by Formulas XIII-XVI.

Deckers catalyst

[Formula XIII]

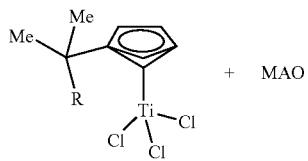 + MAO

S(C6): 86%
Activity 131 083 g/g Ti h

[Formula XIV]

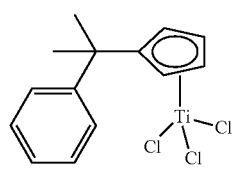

[Formula XV]

[Formula XVI]

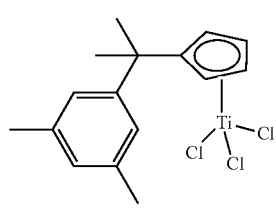

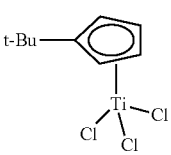

In various embodiments, the ethylene oligomerization catalyst and co-catalyst can be a selective catalyst such as the 1-hexene catalyst of Formula XVII used in a Sumitomo process.

[Formula XVII]

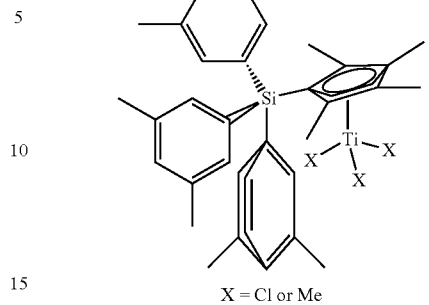

X = Cl or Me

In various embodiments, the ethylene oligomerization catalyst and co-catalyst can be a selective catalyst such as an ethylene oligomerization catalyst system illustrated by Formulas XVIII-XX and used in a Sasol process.

Sasol catalyst

[Formula XVIII]

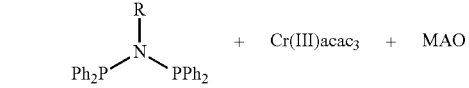

[Formula XIX]

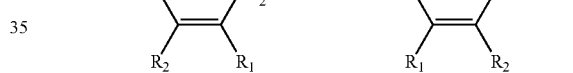

[Formula XX]

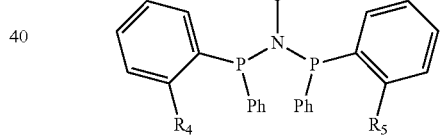

In various embodiments, a co-catalyst can be used with the ethylene oligomerization catalyst system illustrated by Formulas XVIII-XX. In various embodiments, a co-catalyst can be $R_1R_2R_3Al$, where $R_1$, $R_2$, and $R_3$ can be the same or different hydrocarbon groups. In various embodiments, $R_1$, $R_2$, and $R_3$ can be a hydrocarbyl with $C_1$-$C_{100}$ carbon atoms. In various embodiments, $R_1$, $R_2$, and $R_3$ can be a heteroatom X such as a H, F, Cl, Br, O, or N for example or can be a heteroatom containing a ligand such as a $R_4O$, $R_5S$, or $C_6F_5$—. In various embodiments, a co-catalyst can be an aluminoxane having a general formula of $(—Al(R_1)—O—)_n$, where $R_1$ can be a hydrocarbyl ligand that can include a heteroatom X. the heteroatom can be —$F_5C_6$— or $R_2O$. In various embodiments, the co-catalyst can be a solid. In various embodiments, a co-catalyst can be $B(C_6F_5)$ or a salt of $B(C_6F_5)$. In various embodiments, the salt can be $M[B(C_6F_5)_4]$, where M can be $Ph_4N$, $R_1R_2R_3R_4N$, or $R_1R_2R_3R_4P$.

In certain embodiments, the heterogeneous catalytic composition includes an insoluble catalyst and a soluble co-catalyst. The catalyst used in these heterogeneous catalytic composition can be metal-organic frameworks. These are highly porous three dimensional structures formed from metal clusters bridged by organic ligands. An example of such catalytic composition includes soluble MAO and an insoluble catalyst such as nickel-substituted MFU-4l. The material MFU-4l is $Zn_5Cl_4(BTDD)_3$, where $H_2BTDD$ is bis(1H-1,2,3-triazolo[4,5-b],[4',5'-i])dibenzo[1,4]dioxin). A method for producing linear alpha olefins includes the steps of contacting ethylene, in a reactor under oligomerization conditions, with a heterogeneous catalytic composition to produce a first product stream. The heterogeneous catalytic composition contains an insoluble catalyst and a soluble co-catalyst. For example, one such combination includes the soluble MAO and an insoluble catalyst such as nickel-substituted MFU-4l. The method further includes recovering, from the reactor, the first product stream including linear alpha olefins, unreacted ethylene, spent catalytic composition fraction, and usable catalytic composition fraction; separating the usable catalytic composition fraction from the first product stream to produce a second product stream; recovering via fractionation of the second product stream at least one linear alpha olefin product; and recycling the usable catalytic composition fraction to the reactor. The usable catalytic composition is separated from the first product stream using a particle size-based separation process, such as for example, filtration or centrifugation.

In various embodiments, a catalyst and co-catalyst for ethylene oligomerization can be coupled to a solid support such as silica, alumina-silicate, zeolite, metal oxide, clay, polymer, or methylaluminoxane (MAO). In various embodiments, the solid support can be polystyrene. In various embodiments, the solid support can be MAO. In various embodiments, MAO can be a solid support and can be a co-catalyst.

EXAMPLE

Provided here are examples of solid catalytic compositions and the analysis of their dimerization activity and production of polymer deposits on the reactor walls. Tetrahydrofuran (THF) was premixed with the titanium tetrabutoxide (in samples where THF was included) and transferred to a charging cylinder. The solid supports used in this Example were nano-clay (Bentonite), α-Alumina (99.5%), high-purity grade silica gel (Davisil Grade 636), and fumed silica. The solid supports were calcinated at 600° C. for 4 hours before use. The solid supports were individually mixed with the co-catalyst-triethylaluminum-in heptane (1 Molar (M)) and transferred to a charging cylinder. The oligomerization reactions were conducted in an autoclave batch reactor unit (1000 mL volume). In a typical reaction run, the reactor vessel was vacuum purged with ultrapure nitrogen to remove oxygen and moisture. Then, the batch reactor was filled with anhydrous hexane and kept at 50° C. The mixture containing the solid support and triethylaluminum solution in heptane (1 M) was then introduced into the reaction vessel. Then, the pre-mixed solution containing titanium tetrabutoxide and THF was introduced into the reactor. The catalyst solution had a concentration of titanium tetrabutoxide of 1 micromolar. Following introduction of the components of the catalyst system, the reactor was pressurized to 2.3 mega-Pascals (MPa) with ethylene and the temperature of the reactor was set to 53° C. with a stirring rate of 300 rpm. The dimerization reaction was terminated by injecting 2 mL of ethanol after 60 minutes. The reactor was subsequently depressurized. The polymers that stuck to the reactor wall and the stirrers were collected, dried overnight in an oven at 110° C., and weighed. The amount of polymers stuck would be indicative of the fouling that would occur in the reactor vessels.

Table 1 shows the dimerization activity and weight of polymer deposit for reactions which utilized each of the sample catalytic compositions. As is evident by the reaction data of Table 1, the heterogeneous catalyst greatly reduced polymer formation.

TABLE 1

|  | Molar Ratio of Ti:THF:TEAL | Support type | Support weight (g) | Activity (g-C4/ mmol- Ti · h) | Polymer Produced (milli- grams) |
| --- | --- | --- | --- | --- | --- |
| Control | 1:6:7.5 | N/A | N/A | 225.4 | 94 |
| Example 1 | 1:6:7.5 | nano Clay (Bentonite) | 1 | 201 | 35 |
| Example 2 | 1:6:7.5 | α-Alumina | 1 | 191.3 | * |
| Example 3 | 1:6:7.5 | nano Clay (Bentonite) | 2 | 278 | * |
| Example 4 | 1:6:7.5 | Silica gel | 2 | 295 | * |
| Example 4 | 1:6:7.5 | Fumed Silica | 1 | 295 | 38 |

* No polymer could be collected from the reactor wall and stirrers.

As shown in Table 1, when the soluble catalyst and soluble co-catalyst were added to the reaction with no support material in the catalytic composition, then about 94 milligrams (mgs) of the polymer was produced that stuck on the walls and stirrers. In comparison, use of the solid supports like nano-clay, α-Alumina, silica gel, or fumed silica decreased the production of polymers to almost non-collectible levels without any compromise in the activity of the catalytic composition. This example illustrates one of the advantages of the heterogeneous solid catalytic compositions in reduction of fouling of reactor vessels and components, whereby the solid catalytic composition acts as a fouling scavenger by scavenging polymer to prevent deposition on the reactor surfaces.

The preceding description of the disclosed embodiments is provided to enable any person skilled in the art to make or use the disclosed methods and systems. Various modifications to these embodiments will be readily apparent to those skilled in the art, and the generic principles defined here may be applied to other embodiments without departing from the spirit or scope of the disclosure. Thus, the disclosure is not intended to be limited to the embodiments shown here but is to be accorded the widest scope consistent with the following claims and the principles and novel features disclosed here.

What is claimed is:

1. A method for producing linear alpha olefins, comprising:
   contacting ethylene, in a reactor under oligomerization conditions, with a heterogeneous catalytic composition to produce a first product stream, the heterogeneous catalytic composition containing a catalyst, a co-catalyst, and a solid support;
   recovering, from the reactor, the first product stream including linear alpha olefins, unreacted ethylene, spent catalytic composition fraction, and usable catalytic composition fraction;
   separating the spent catalytic composition fraction from the first product stream using a particle size-based separation process to produce a second product stream;
   separating the usable catalytic composition fraction from the second product stream to produce a third product stream;

fractionating the third product stream to separate at least one linear alpha olefin product; and recycling the usable catalytic composition fraction to the reactor;

wherein the spent catalytic composition fraction comprises a polymer byproduct of the oligomerization, said spent catalytic composition fraction has a size distribution in the range of 30-500 microns;

wherein the usable catalytic composition fraction has a size distribution of less than 30 micron, and wherein the particle size-based separation process is filtration or centrifugation.

2. The method of claim 1, wherein the catalyst is one or more of an aluminum-based catalyst and a transition metal-based catalyst.

3. The method of claim 2, wherein the transition metal is at least one member of the group consisting of nickel, titanium, zirconium or chromium.

4. The method of claim 1, wherein the catalyst is one or more of a phosphorus-oxygen chelate of nickel (I) complex, a zirconium-aluminum alkyl halide, a tri-alkyl aluminum compound, a titanate-aluminum alkyl compound, a chromium(III) complex bearing imino-furfural ligands, a titanium butoxidetriethylaluminum compound, a cyclopentadienyl-arene complex, and other ethylene oligomerization catalysts.

5. The method of claim 1, wherein the co-catalyst is methylaluminoxane.

6. The method of claim 1, wherein the catalyst is metal-organic framework-based catalyst.

7. The method of claim 1, wherein the solid support is at least one member of the group consisting of silica, clay, zeolite, aluminosilicate, and solid aluminoxane.

8. The method of claim 1, wherein the solid support and the co-catalyst comprise methylaluminoxane.

9. The method of claim 1, wherein the co-catalyst is at least one member of the group consisting of boron-based complex and organoaluminum compounds represented by the formula $R_1R_2R_3A$, wherein A is either boron or aluminum, and $R_1$, $R_2$, and $R_3$ are hydrocarbyl groups with or without heteroatom substitutions.

10. The method of claim 1, where the co-catalyst is at least one member of the group consisting of $B(C_6F_5)_3$, $Ph_3C(B(C_6F_5)_4$, and $[PhMe_2NH][B(C_6F_5)_4]$ or salts thereof.

11. A method for producing linear alpha olefins, comprising:

supplying a catalytic composition, containing a soluble catalyst and a soluble co-catalyst linked to a solid support, and ethylene to a reactor under oligomerization conditions, to produce a first product stream;

recovering, from the reactor, the first product stream including linear alpha olefins, unreacted ethylene, spent catalytic composition fraction, and usable catalytic composition fraction;

separating the spent catalytic composition fraction from the first product stream using a particle size-based separation process to produce a second product stream;

separating the usable catalytic composition fraction from the second product stream to produce a third product stream;

fractionating the third product stream to separate at least one linear alpha olefin product; and recycling the usable catalytic composition fraction to the reactor;

wherein the spent catalytic composition fraction comprises a polymer byproduct of the oligomerization, said spent catalytic composition fraction has a size distribution in the range of 30-500 microns;

wherein the usable catalytic composition fraction has a size distribution of less than 30 micron, and wherein the particle size-based separation process is filtration or centrifugation.

12. The method of claim 11, wherein the solid support is at least one member of the group consisting of silica, clay, zeolite, aluminosilicate, and solid aluminoxane.

13. The method of claim 11, wherein the catalyst is one or more of an aluminum-based catalyst and a transition metal-based catalyst.

14. The method of claim 11, wherein the co-catalyst is at least one member of the group consisting of boron-based complex and organoaluminum compounds represented by the formula $R_1R_2R_3A$, wherein A is either boron or aluminum, and $R_1$, $R_2$, and $R_3$ are hydrocarbyl groups with or without heteroatom substitutions.

15. The method of claim 14, where the boron based complex is at least one member of the group consisting of $B(C_6F_5)_3$, $Ph_3C(B(C_6F_5)_4$, and $[PhMe_2NH][B(C_6F_5)_4]$ or salts thereof.

* * * * *